(12) United States Patent
Kaushik et al.

(10) Patent No.: US 9,902,751 B2
(45) Date of Patent: Feb. 27, 2018

(54) PROCESS FOR THE PREPARATION OF EMPAGLIFLOZIN

(71) Applicant: Mylan Laboratories Ltd., Hyderabad (IN)

(72) Inventors: Vipin Kumar Kaushik, Hyderabad (IN); Jagan Mohana Chary Tummanepally, Hyderabad (IN); Jayaram Pothani, Hyderabad (IN); Ramarao Dodda, Hyderabad (IN)

(73) Assignee: Mylan Laboratories Limited (IN)

( * ) Notice: Subject to any disclaimer, the term of this patent is extended or adjusted under 35 U.S.C. 154(b) by 0 days.

(21) Appl. No.: 15/105,620

(22) PCT Filed: Dec. 29, 2014

(86) PCT No.: PCT/IB2014/067380
§ 371 (c)(1),
(2) Date: Jun. 17, 2016

(87) PCT Pub. No.: WO2015/101916
PCT Pub. Date: Jul. 9, 2015

(65) Prior Publication Data
US 2016/0318965 A1  Nov. 3, 2016

(30) Foreign Application Priority Data
Dec. 30, 2013 (IN) .......................... 6139/CHE/2013

(51) Int. Cl.
| C07H 7/06 | (2006.01) |
| C07H 1/00 | (2006.01) |
| C07H 7/04 | (2006.01) |
| C07H 15/04 | (2006.01) |
| C07D 407/12 | (2006.01) |
| C07H 23/00 | (2006.01) |
| C07D 307/20 | (2006.01) |

(52) U.S. Cl.
CPC .............. *C07H 7/06* (2013.01); *C07D 307/20* (2013.01); *C07D 407/12* (2013.01); *C07H 1/00* (2013.01); *C07H 7/04* (2013.01); *C07H 15/04* (2013.01); *C07H 23/00* (2013.01); *Y02P 20/55* (2015.11)

(58) Field of Classification Search
None
See application file for complete search history.

(56) References Cited

U.S. PATENT DOCUMENTS

| 6,303,661 B1 | 10/2001 | Demuth |
| 6,414,126 B1 | 7/2002 | Ellsworth |
| 6,488,962 B1 | 12/2002 | Berner |
| 6,515,117 B2 | 2/2003 | Ellsworth |
| 6,890,898 B2 | 5/2005 | Bachovchin |
| 7,078,381 B2 | 7/2006 | Bachovchin |
| 7,371,732 B2 | 5/2008 | Eickelmann |
| 7,407,955 B2 | 8/2008 | Himmelsbach |
| 7,459,428 B2 | 12/2008 | Bachovchin |
| 7,579,449 B2 | 8/2009 | Eckhardt |
| 7,683,160 B2 | 3/2010 | Eckhardt |
| 7,713,938 B2 | 5/2010 | Himmelsbach |
| 7,723,309 B2 | 5/2010 | Himmelsbach |
| 7,772,191 B2 | 8/2010 | Eckhardt |
| 8,119,648 B2 | 2/2012 | Himmelsbach |
| 8,178,541 B2 | 5/2012 | Himmelsbach |
| 8,486,453 B2 | 7/2013 | Chen |
| 8,551,957 B2 | 10/2013 | Dugi |
| 8,791,069 B1 | 7/2014 | Sung |

(Continued)

FOREIGN PATENT DOCUMENTS

| IN | 1985MUM2013 A | 5/2015 |
| WO | 2006120208 | 11/2006 |

(Continued)

OTHER PUBLICATIONS

Written Opinion and Search Report for corresponding International Application No. PCT/IB2014/67380 dated Mar. 24, 2015.

(Continued)

*Primary Examiner* — Layla D Berry

(57) ABSTRACT

An improved process for the preparation of empagliflozin is disclosed. Novel intermediates of formulas (13) and (14) for the preparation of empagliflozin are also disclosed, wherein $R^1$ and $R^2$ are independently hydrogen or hydroxyl protecting groups.

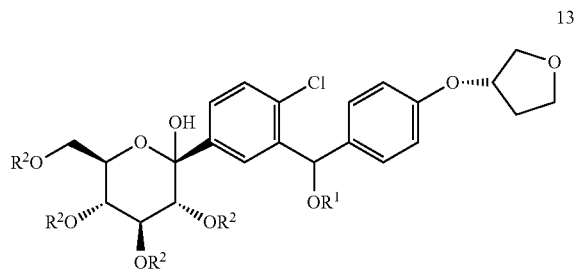

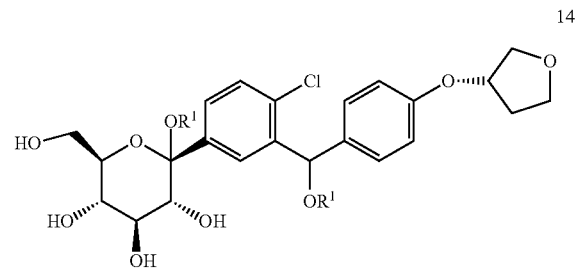

14 Claims, No Drawings

(56) References Cited

U.S. PATENT DOCUMENTS

| | | |
|---|---|---|
| 8,802,842 B2 | 8/2014 | Weber |
| 8,952,139 B2 | 2/2015 | Henschke et al. |
| 9,024,010 B2 | 5/2015 | Weber |
| 9,056,112 B2 | 6/2015 | Haldar et al. |
| 9,127,034 B2 | 9/2015 | Eckhardt |
| 9,174,971 B2 | 11/2015 | Farina |
| 9,193,751 B2 | 11/2015 | Xu et al. |
| 9,464,043 B2 | 10/2016 | Roberge et al. |
| 9,725,478 B2 | 8/2017 | Xu et al. |
| 2005/0187168 A1 | 8/2005 | Eickelmann et al. |
| 2005/0209166 A1 | 9/2005 | Eckhardt et al. |
| 2010/0298243 A1 | 11/2010 | Manuchehri et al. |
| 2011/0014284 A1 | 1/2011 | Eisenreich et al. |
| 2011/0236477 A1 | 9/2011 | Schneider et al. |
| 2013/0064887 A1 | 3/2013 | Ito et al. |
| 2013/0303446 A1 | 11/2013 | Hamilton et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0243517 A1 | 8/2014 | Deshpande et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2014/0378398 A1 | 12/2014 | Hamilton et al. |
| 2015/0218200 A1 | 8/2015 | Weber et al. |
| 2015/0322053 A1 | 11/2015 | Eckhardt et al. |
| 2016/0000816 A1 | 1/2016 | Broedl et al. |
| 2016/0030385 A1 | 2/2016 | Manuchehri et al. |
| 2016/0038523 A1 | 2/2016 | Broedl et al. |
| 2016/0038524 A1 | 2/2016 | Broedl et al. |
| 2016/0038525 A1 | 2/2016 | Broedl et al. |
| 2016/0067227 A1 | 2/2016 | Broedl et al. |
| 2016/0158264 A1 | 6/2016 | Eickelmann et al. |
| 2016/0235680 A1 | 8/2016 | Ito et al. |

FOREIGN PATENT DOCUMENTS

| | | |
|---|---|---|
| WO | 2008055940 | 5/2008 |
| WO | 2008077009 | 6/2008 |
| WO | 2008077099 | 6/2008 |
| WO | 2011039107 | 4/2011 |
| WO | 2013007557 | 1/2013 |
| WO | 2015012110 | 1/2015 |
| WO | 2015101916 | 9/2015 |
| WO | 2015173584 | 11/2015 |
| WO | 2015177083 | 11/2015 |
| WO | 2016016770 | 2/2016 |
| WO | 2016016772 | 2/2016 |
| WO | 2016051368 | 4/2016 |
| WO | 2016128995 | 8/2016 |
| WO | 2016174155 | 11/2016 |
| WO | 2017046730 | 3/2017 |
| WO | 2017093419 | 6/2017 |
| WO | 2017098481 | 6/2017 |

OTHER PUBLICATIONS

Database Caplus [online] Chemical Abstracts Service, Columbus, Ohio, US; May 29, 2015 (May 29, 2015), Dwivedi, Shriprakash Dhar et al: "Process for the preparation of amorphous form of empagliflozin", XP002750955, retrieved from STN Database accession No. 2015:947037.

R Grempler et al: "Empagliflozin, a novel selective sodium glucose cotransporter-2 (SGLT-2) inhibitor: characterisation and comparison with other SGLT-2 inhibitors Introduction", Diabetes Obesity and Metabolism, vol. 14, 2012, pp. 83-90, XP055228524.

PROCESS FOR THE PREPARATION OF EMPAGLIFLOZIN

CROSS-REFERENCE TO RELATED APPLICATIONS

This application is a national stage filing of PCT Application No. PCT/IB2014/067380, filed Dec. 19, 2014, which in turn claimed priority to and the benefit of priority to 6139/CHE/2013, filed on Dec. 30, 2013.

BACKGROUND OF THE INVENTION

Field of the Invention

The present disclosure relates to a novel process for the preparation of empagliflozin. The present disclosure also relates to novel intermediates in the preparation of empagliflozin.

Background of the Invention

Empagliflozin is an inhibitor of the $Na^+$-glucose cotransporter 2 (SGLT2) and is marketed under the proprietary name JORDIANCE®. It is indicated for prevention and/or treatment of metabolic disorders, particularly type-2 diabetes. Empagliflozin belongs to a class of pyranosyl-oxy-substituted benzene derivatives and has an enhanced inhibitory effect on SGLT2 in vitro and in vivo, while having improved pharmacological or pharmacokinetic properties when compared with other type-2 diabetic medications.

Empagliflozin is chemically named as (1S)-1,5-anhydro-1-C-[4-chloro-3-[[4-[[(3S)-tetrahydro-3-furanyl] oxy] phenyl] methyl] phenyl]-D-glucitol and has the following structural (I):

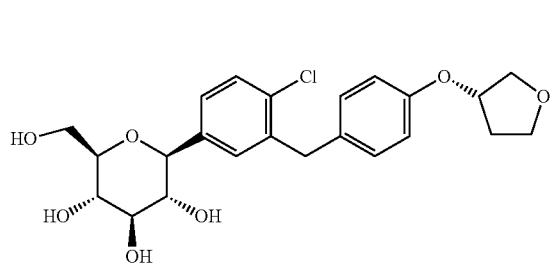

I

U.S. Pat. No. 7,579,449, which is hereby incorporated by reference, discloses empagliflozin, stereoisomers of empagliflozin, mixtures and salts thereof, and a pharmaceutical composition containing empagliflozin.

Disclosed herein is a process for the preparation of empaglofilozin that provides multiple improvements over the prior art.

SUMMARY OF THE INVENTION

In one aspect, the disclosure provides a process for the preparation of empagliflozin, comprising the steps of: reducing a compound of formula 14 in the presence of a reducing agent to obtain empagliflozin of formula I, wherein $R^1$ is hydrogen or hydroxyl protecting groups

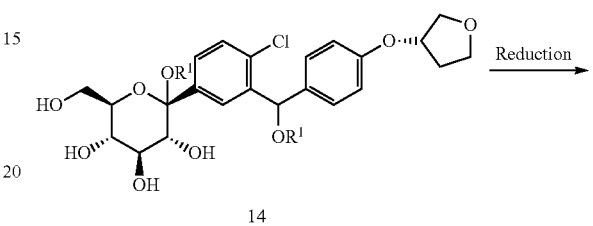

14

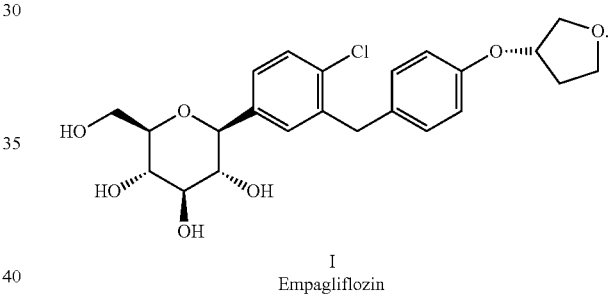

I
Empagliflozin

In another aspect, the disclosure provides a process for the preparation of empagliflozin, comprising the steps of:
hydrolyzing a compound of formula 13, followed by selective hydroxyl protection to obtain a compound formula 14, wherein $R^1$ and $R^2$ are independently hydrogen or hydroxyl protecting groups

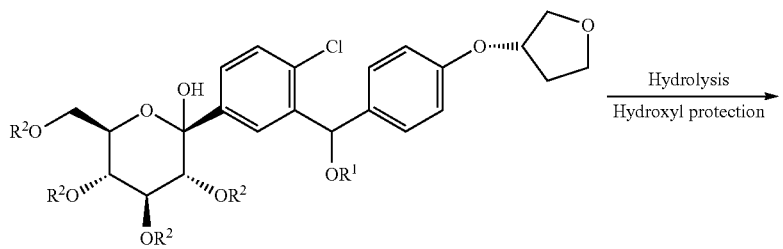

13

-continued

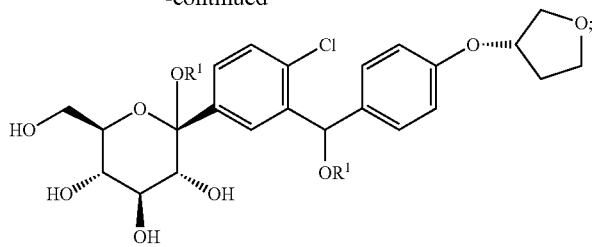

14 and reducing the compound of formula 14 in the presence of a reducing agent to obtain empagliflozin of formula I.

In another aspect, the disclosure provides a process for the preparation of empagliflozin, comprising the steps of:

reacting a compound of formula 12' with a compound of formula 1 to produce a compound of formula 13, wherein $R^1$ and $R^2$ are independently hydroxyl protecting groups

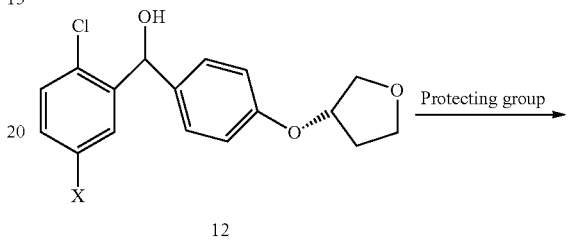

12

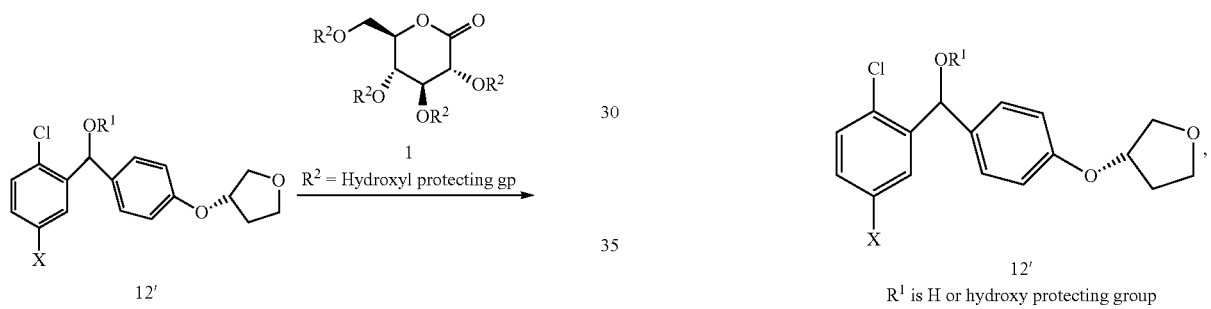

12'
$R^1$ is H or hydroxy protecting group reacting the compound of formula 12' with a compound of formula 1 to produce the compound of formula 13, wherein $R^1$ and $R^2$ are independently hydroxyl protecting groups;

hydrolyzing a compound of formula 13, followed by selective hydroxyl protection to obtain a compound formula 14, wherein $R^1$ and $R^2$ are independently hydrogen or hydroxyl protecting groups; and reducing the compound of formula 14 in the presence of a reducing agent to obtain empagliflozin of formula I.

Another aspect of the present disclosure is to provide a novel process for the preparation of empagliflozin comprising the steps of;

a) reacting formula 12 with a protecting group to make formula 12', b) reacting formula 12' with formula 1 to make formula 13, c) hydrolyzing formula 13, followed by selective hydroxyl protection to make formula 14, and d) reducing formula 14 in the presence of reducing agent to obtain empagliflozin of formula I.

In another aspect of the present disclosure provides a process for the preparation of formula 12 by reacting a compound of formula 10 with a compound of formula 11 in the presence of a base

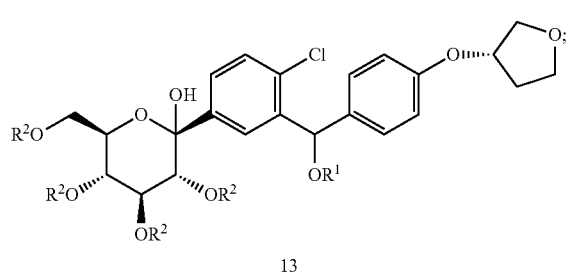

13 hydrolyzing the compound of formula 13, followed by selective hydroxyl protection to obtain a compound formula 14, wherein $R^1$ and $R^2$ are independently hydrogen or hydroxyl protecting groups;

and reducing the compound of formula 14 in the presence of a reducing agent to obtain empagliflozin of formula I.

In another aspect, the disclosure provides a process for the preparation of empagliflozin, comprising the steps of:

reacting a compound of formula 12 with a hydroxyl protecting agent to obtain the compound of formula 12', wherein X is a halogen and $R^1$ is a hydroxyl protecting group

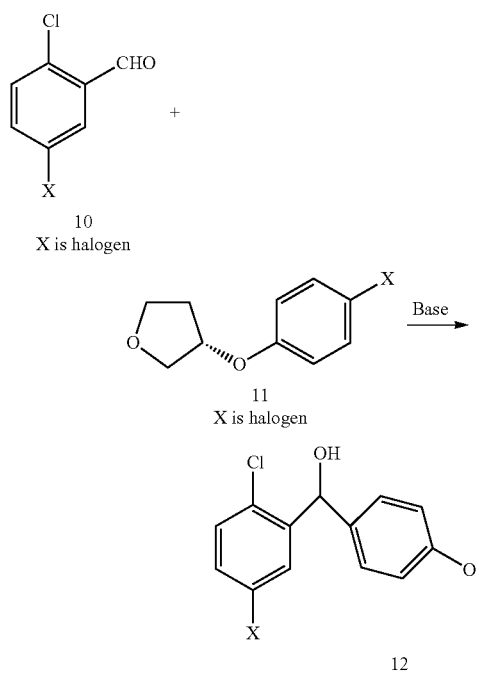

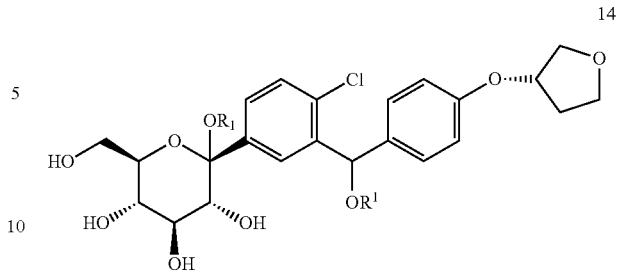

wherein TMS is a trimethylsilyl group, and wherein $R^1$ and $R^2$ are independently hydrogen or a hydroxyl protecting groups.

DETAILED DESCRIPTION OF THE INVENTION

It is to be understood that the description of the present disclosure has been simplified to illustrate elements that are relevant for a clear understanding of the disclosure, while eliminating, for purposes of clarity, other elements that may be well known.

The present disclosure encompasses novel synthetic schemes for the preparation of empagliflozin. Within the context of the present disclosure, novel intermediates are generated as part of the novel synthetic routes. Together, these schemes and intermediates provide an improved, efficient method for the synthesis of empagliflozin.

Yet another aspect of the present disclosure is to provide novel intermediates of empagliflozin, shown below as formula 12a, 12'a, 13, and 14.

The main embodiment of the present disclosure provides a process for the preparation of empagliflozin, which is shown below in Scheme-A.

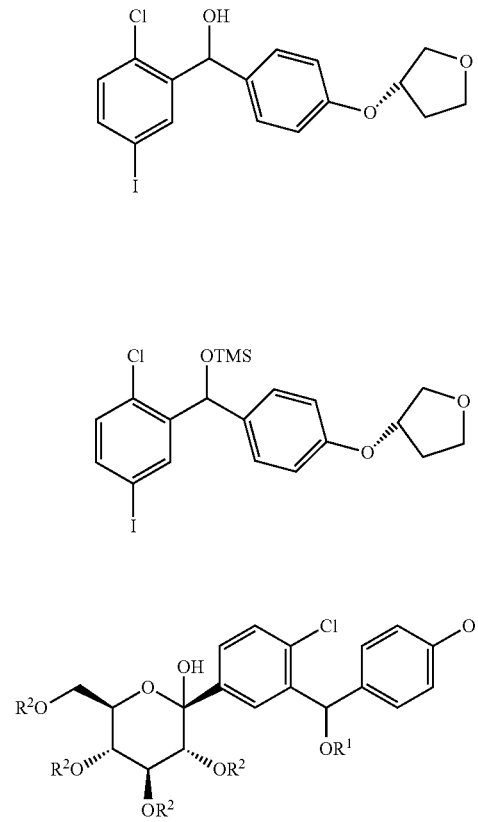

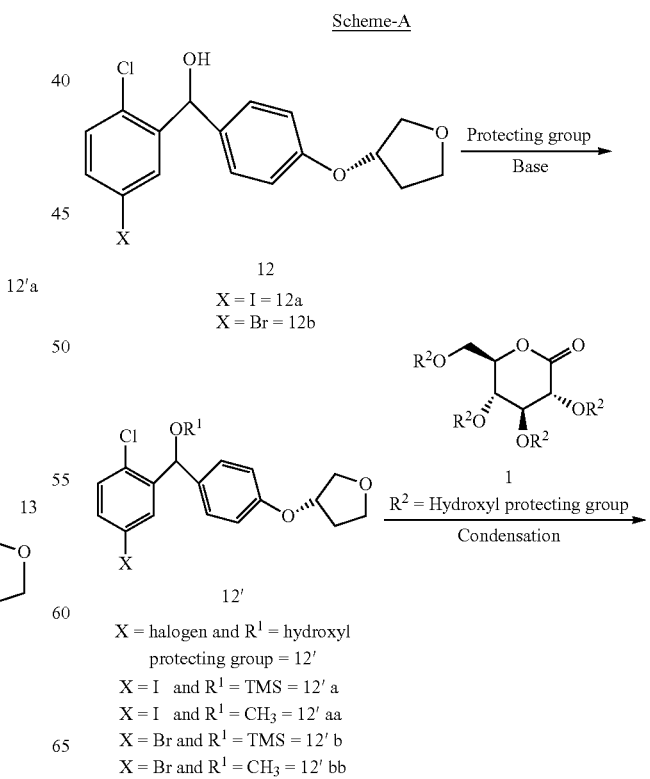

-continued

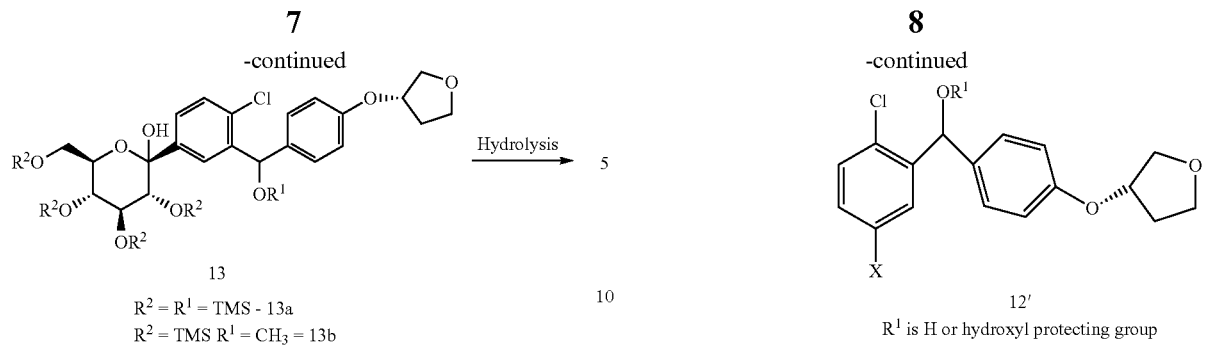

13
$R^2 = R^1 = TMS$ - 13a
$R^2 = TMS$ $R^1 = CH_3$ = 13b

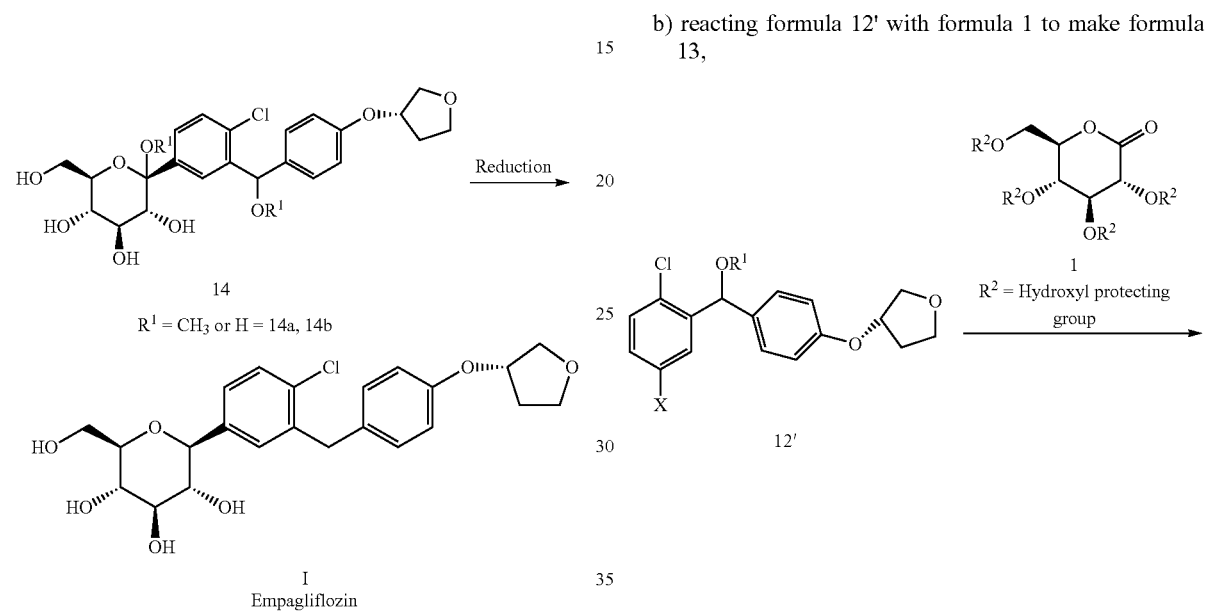

14
$R^1 = CH_3$ or H = 14a, 14b

I
Empagliflozin

One embodiment of the present disclosure provides a process for the preparation of empagliflozin which may include the following steps:

a) reacting formula 12 with a protecting agent to make formula 12',

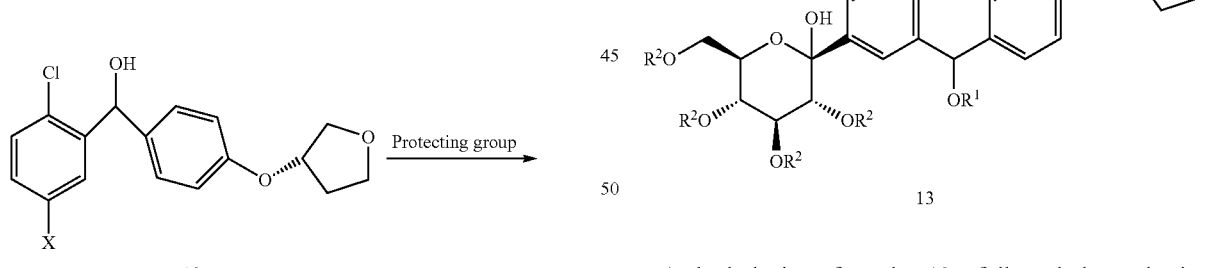

-continued

12'
$R^1$ is H or hydroxyl protecting group b) reacting formula 12' with formula 1 to make formula 13,

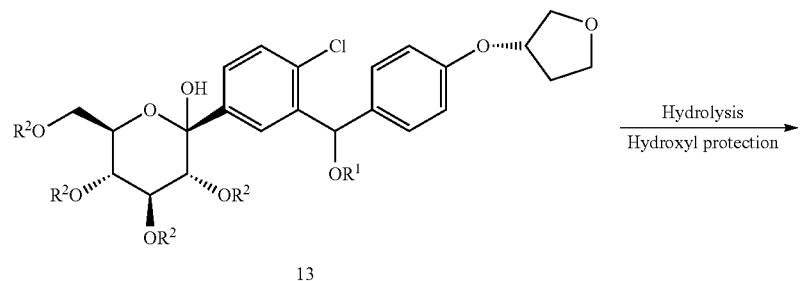

c) hydrolyzing formula 13, followed by selective hydroxyl protection to make formula 14, and

13

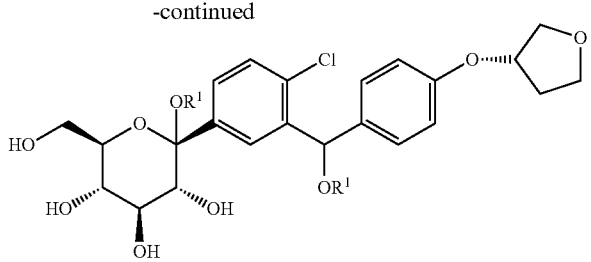

14 d) reducing formula 14 in the presence of reducing agent to obtain empagliflozin of formula I.

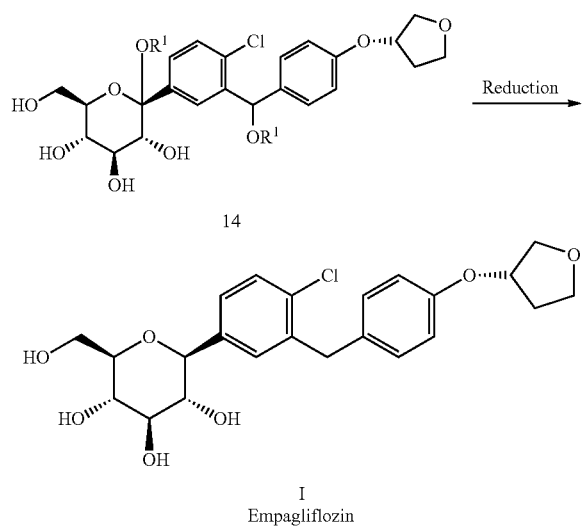

According to the present disclosure, formula 12 is first dissolved in a solvent. The solvent may be, as examples, ethanol, isopropanol, dichloromethane, chloroform, carbon tetrachloride, or mixtures thereof. In one example, the solvent is dichloromethane. This solution may then be reacted with a hydroxyl protecting agent (e.g., trimethyl silyl chloride, tertiary butyl dimethyl silyl chloride, benzyl chloride, benzoyl chloride or acetyl chloride) at a temperature of 0° C. to 30° C. for about 1-2 hours to provide formula 12'. This reaction may be carried out in the presence of a base or an acid. Within the context of the present disclosure, temperature and reaction conditions may vary and can be dependent upon the nature of the hydroxyl protecting group. However, one of skill in the art will easily recognize appropriate conditions and identify those most useful without undue experimentation. In some embodiments, the hydroxyl protecting group $R^1$ may be for example, benzyl, benzoyl, $C_{1-12}$ alkyl, silyl, trimethylsilyl (TMS), tertiary butyl dimethyl silyl, allyl, or sulfonyl. Within the context of present disclosure, it has been found that silyl or $C_1$-$C_{12}$ alkyl are particularly used for hydroxyl protecting group for this disclosure. When using a silyl group as a protecting group, the reaction may be carried out at about 0° C. to 5° C. in the presence of a base. In such embodiments, the reaction temperature may be about 25° C. to 35° C. and occur in the presence of an acid.

Within the context of the present disclosure, the base employed when reacting formula 12 with a silyl-based hydroxyl protecting agent may include, as examples, triethylamine, diisopropylamine, or pyridine. In certain embodiments, it has been found that triethylamine is particularly useful base.

Within the context of the present disclosure, the acid employed when reacting formula 12 with an alkyl-based hydroxyl protecting agent includes, as examples, methane sulfonic acid, p-toluene sulfonic acid, acetic acid, and oxalic acid. In certain embodiments, the acid is methane sulfonic acid.

According to the present embodiment, formula 12' may then be reacted with formula 1 in a solvent at about −80° C. to about −60° C. for about 1-2 hours in the presence of a base to obtain formula 13. This solvent may be, for example, tetrahydrofuran, dimethylformamide, acetonitrile, toluene, or mixtures thereof. Within the context of the present disclosure, it has been found that n-butyl lithium is particularly useful acid for alkyl protection.

According to the present disclosure, Formula 1 may be a variety of different compounds, depending on the $R^2$ hydroxyl protecting group. Within the context of the present disclosure, $R^2$ may be, as examples, trimethyl silyl, tertiary butyl dimethyl silyl, benzyl, benzoyl, or acetyl.

According to the present disclosure, formula 13 may then be hydrolyzed to remove the $R^2$ protecting groups, and then reacted to protect the hydroxyl group in formula 13. This reaction may be performed at 20° C.-40° C. for about 12-16 hours to obtain formula 14. This reaction may also be performed in the presence of an acid and an alcohol solvent, which may be, for example, methanol, ethanol, isopropanol, or mixtures thereof. Within the context of the present disclosure, the acid employed in this step of the reaction may include, as examples, methane sulfonic acid, p-toluene sulfonic acid, acetic acid, and oxalic acid. In certain embodiments, it has been found that methane sulfonic acid is particularly useful acid for hydrolysis.

According to the present disclosure, empagliflozin of formula I is prepared by reducing formula 14 in a solvent with a reducing agent. The solvent may be, as examples dichloromethane, chloroform, acetonitrile, toluene, tetrahydrofuran, or mixtures thereof. The addition of the reducing agent may be carried out at about −50° C. to −30° C., slowly raised to about 30° C., and maintained at that temperature for about 3-5 hours or until the completion of the reaction by HPLC.

Within the context of the present disclosure, the reducing agent employed in this reaction step may include, for example, triethylsilane, boron trifluoride diethyl etherate, or mixtures thereof. In certain embodiments, the reducing agent istriethylsilane or boron trifluoride diethyl etherate mixture.

Within the context of the present disclosure, hydroxyl protecting group employed may include, for example, benzyl, benzoyl, $C_{1-4}$ alkyl, silyl, tertiary butyl dimethyl silyl, allyl, or sulfonyl. According to the present disclosure, the hydroxyl protecting group benzyl, benzoyl or sulfonyl groups are optionally substituted with alkyl, halogen, tri (C1-6 alkyl)silyl, nitro, aryl or heteraryl groups. One of ordinary skill in the art will appreciate that each protecting group will be employed using appropriate reagents and reaction conditions.

According to the present disclosure, the obtained compound may then be purified in a solvent to produce substantially pure empagliflozin. Within the context of the present disclosure, the solvent employed for crystallization may include, for example, isopropyl acetate, ethyl acetate, methyl acetate, or mixtures thereof. In some embodiments, it has been found that isopropyl acetate is a particularly useful solvent. Within the context of the present disclosure, the temperature employed for purification may range from about 25° C. to about 60° C. In certain embodiments, it has been found that 45° C.-50° C. is a particularly suitable temperature.

Yet another embodiment of the present disclosure provides a process for the preparation of formula 12. Formula 12 may be prepared by reacting formula 10 with formula 11 in the presence of a base.

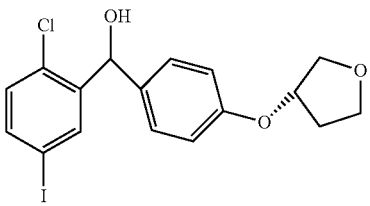

12a

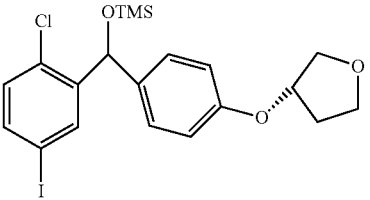

12'a

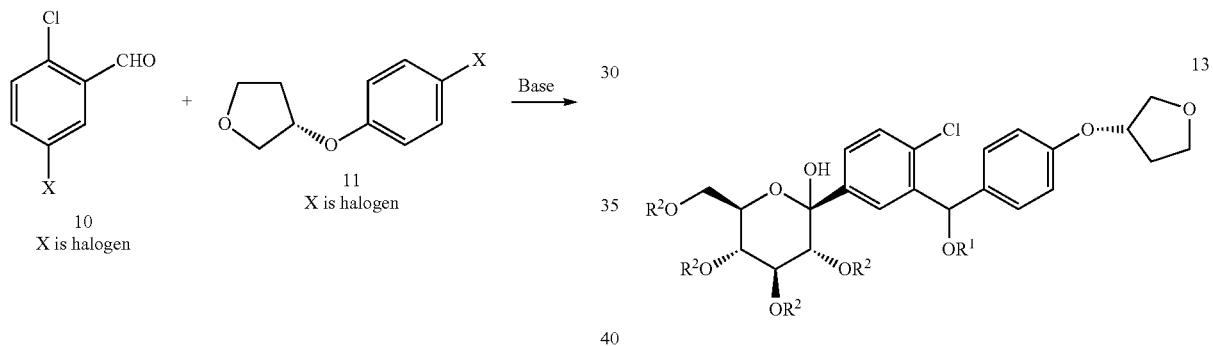

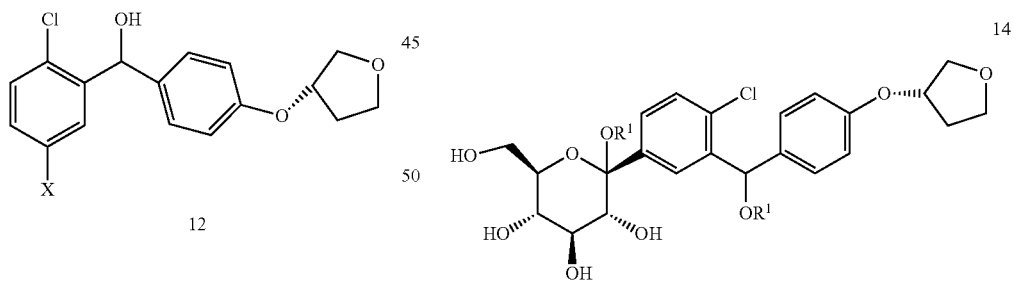

According to the present disclosure, formula 12 may be prepared by reacting formula 10 with formula 11 in a solvent in the presence of a base at a temperature of −80° C. to 70° C. for about 1-2 hours. The solvent may be, as examples, tetrahydrofuran, dimethylformamide, dioxane, or mixtures thereof. Within the context of the present disclosure, the base may include, as examples, n-butyl lithium, isopropyl magnesium chloride lithium chloride, magnesium chloride, Tertiary butyl magnesium chloride in certain embodiments, it has been found that n-butyl lithium is a particularly useful base.

Another aspect of the present disclosure provides novel intermediates of empagliflozin, shown below:

The novel intermediates presently disclosed may be characterized by NMR analysis. The analysis was performed on a Bruker 300 MHz Avance NMR spectrometer equipped with 5 mm BBI probe. The compounds were dissolved in DMSO-d6. The data were collected and processed by Topsin-NMR software.

Yet another aspect of the present disclosure is to provide a process for the preparation of empagliflozin, as depicted in the following synthetic Scheme-B.

Scheme-B
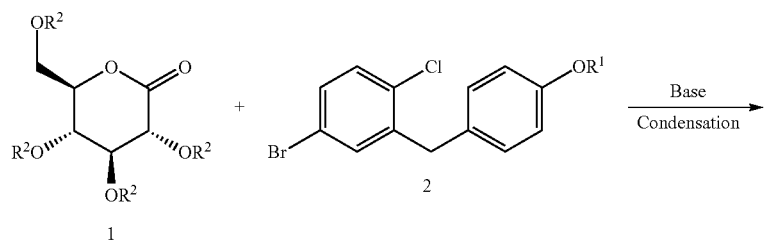
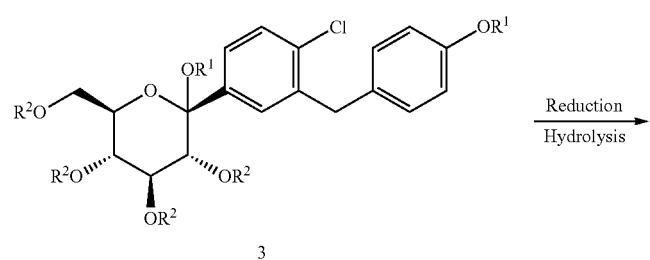
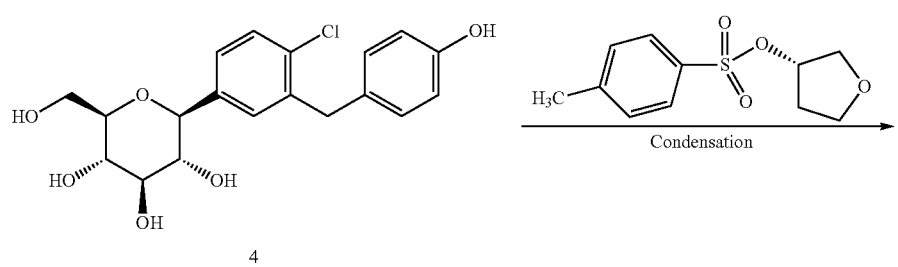
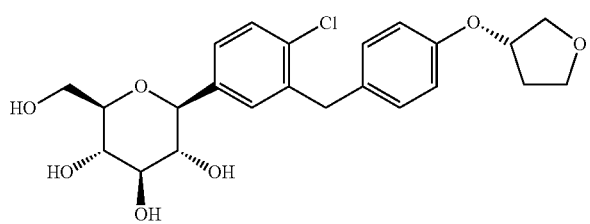
I
Empagliflozin
$R^1 = R^2 =$ Hydroxyl protecting group Yet another aspect of the present disclosure is to provide a process for the preparation of intermediate of Formula-12 as depicted in the following synthetic Scheme-C.

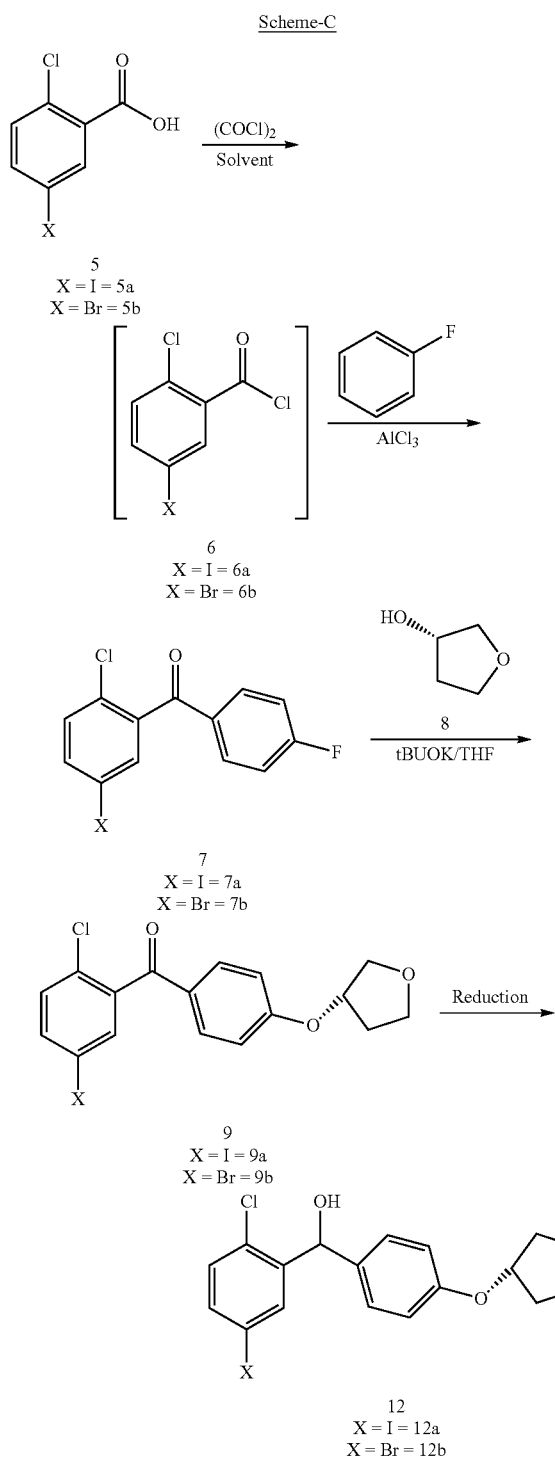

In view of the above description and the examples below, one of ordinary skill in the art will be able to practice the disclosure as claimed without undue experimentation. The foregoing will be better understood with reference to the following examples that detail certain procedures for the preparation of molecules, compositions and formulations according to the present disclosure. All references made to these examples are for the purposes of illustration. The following examples should not be considered exhaustive, but merely illustrative of only a few of the many aspects and embodiments contemplated by the present disclosure.

EXAMPLES

Example 1: Preparation of Formula 7b

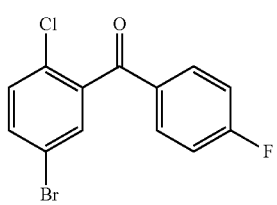

Oxalyl chloride (86.2 g, 0.67 moles) was added to a slurry of 5-bromo-2-chlorobenzoic acid (100 g, 0.42 moles) and a catalytic amount of N,N-dimethylformamide (5 mL) in fluorobenzene (250 mL), over about 60 minutes at 15-25° C. under nitrogen atmosphere. The mixture was stirred at 21-25° C. After completion of reaction, the reaction mass was concentrated to remove excess oxalyl chloride by distillation. The obtained residue was diluted with fluorobenzene (125 mL) and cooled to 15-25° C. Thereafter, aluminum chloride was added to the reaction mass portion-wise (64.6 g, 0.48 moles), keeping the reaction mass temperature below 25° C. After completion of the reaction, the reaction was quenched into precooled dilute hydrochloric acid at 5-25° C. After stirring the reaction mass for 60 minutes at 20-25° C., the reaction mass was extracted with methylene chloride (once with 500 mL, then with 250 mL). The combined organic layers were washed with 10% aqueous sodium hydroxide solution (250 mL), water (350 mL), and 10% aqueous sodium chloride solution (350 mL) sequentially. Thereafter, the organic layer was concentrated and obtained residue was treated with n-heptane to precipitate formula 7b as a white solid (110 g).

Example 2: Preparation of Formula 9b

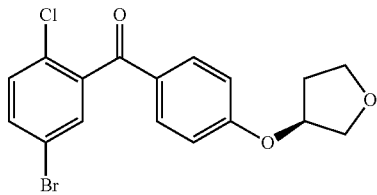

A solution of potassium tert-butoxide (53.6 g, 0.477 mole) in tetrahydrofuran (450 mL) was slowly added to a mixture of formula 7b (100 g, 0.32 mole) and (S)-tetrahydrofuran-3-ol (31.5 m g, 0.351 mole) in tetrahydrofuran (260 mL) over a period of 90 minutes at 2-6° C. The reaction mass was maintained at 7-10° C. to complete the reaction. After completion of the reaction, precooled water (5-18° C., 285 mL) was added to quench the reaction. The reaction mass was extracted with methyl tert-butyl ether (once with 285 mL, then with 145 mL) to the reaction mixture at 20-25° C. Thereafter, the combined organic layers were washed with aqueous sodium chloride solution (10%, 290 mL) and concentrated under reduced pressure. The residue was crystallized in isopropyl acetate (150 mL) to get formula 9b as a solid (90 g).

Example 3: Preparation of Formula 12b

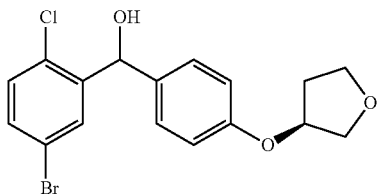

12b

Formula 9b (100 g) was added to ethanol (800 mL). Sodium borohydride (14.9 g, 0.39 moles) was then added lot-wise at 20-25° C. After completion of the reaction, the pH of reaction mass was adjusted to 6.5-7.5 with dilute hydrochloric acid, keeping the temperature below 20° C. After stirring for 60 minutes, salts were separated out by filtration and the residue was washed with ethanol (100 mL). This filtrate was concentrated and diluted with water (1000 mL). Thereafter, the product was extracted with methyl tert-butyl ether (500 mL) at 20-25° C. The organic layer was washed with water (300 mL) and sodium chloride (10%, 300 mL) and concentrated under reduced pressure to yield formula 12b as a viscous liquid (98 g) which tends to solidify on standing (98 g).

Example 4: Preparation of Formula 12b

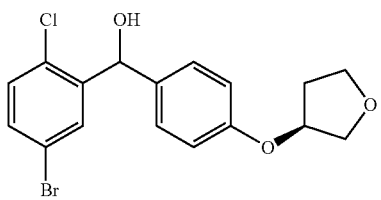

12b

Formula 10 (20 g) and (S)-3-(4-bromophenoxy) tetrahydrofuran (33.2 g) were dissolved in tetrahydrofuran (160 mL) at 25-35° C. under nitrogen atmosphere. This reaction mass was cooled to −75 to −70° C. over a period of 30-60 minutes under nitrogen atmosphere. N-butyl lithium (15% w/w in hexane) (99 mL, 0.16 moles) was then added over a period of 60-90 minutes at same temperature. After completion of the reaction, hydrochloric acid (1 N, 150 mL) was added to the reaction mass over a period of 30 minutes at −70 to −78° C. to quench the reaction. Thereafter, the temperature of reaction mass was raised to 20-25° C. and the product was extracted with ethyl acetate (150 mL). The organic layer was concentrated under reduced pressure to yield the formula 12b as a viscous liquid (46 g), which may solidify upon standing (46 g).

Example 5: Preparation of Formula 12'b

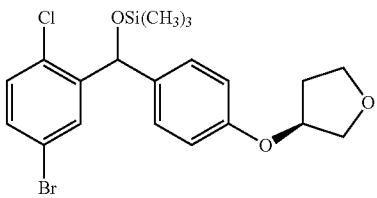

12'b

Formula 12 (100 g, 0.26 moles) and triethylamine (59.3 g, 0.59 moles) were added to methylene chloride (900 mL) at 0-5° C. Thereafter, trimethylsilyl chloride (42.2 g, 0.39 moles) was added slowly over a period of 60 minutes, maintaining the mixture at the same temperature. After addition, the temperature of the reaction mass was raised to 30-35° C. and stirred until the reaction completed. After completion, the reaction mass was again cooled to 0-10° C. and slowly diluted with water (500 mL), keeping the temperature below 15° C. After separating out the organic layer, the product was extracted again from aqueous layer by adding methylene chloride (250 mL). The combined organic layers were washed with water (500 mL) and sodium dihydrogen phosphate (10% 400 mL). The organic layer was separated once again, after washing once with water (500 mL), and again with 10% aqueous sodium chloride (400 mL). The organic layer was concentrated under reduced pressure to yield formula 12'b as a viscous liquid (95 g).

Example 6: Preparation of Formula 12'bb

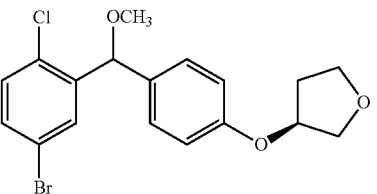

12'bb

Formula 12 (50 g) was added to methanol (300 mL) at 20-25° C. Methane sulfonic acid (16.2 g) diluted in methanol (20 mL) was then added slowly at 20-30° C. After completion of reaction, the pH of reaction mass was adjusted to 7.3 with aqueous sodium bicarbonate solution. Thereafter, the reaction mass was concentrated under reduced pressure while maintaining the temperature below 50° C. The obtained residue was diluted with water (400 mL) and the product was extracted with toluene (2×250 mL). The combined organic layers were washed with 10% aqueous sodium chloride and concentrated to yield formula 12'bb (45 g).

Example-7

Preparation of Formula 7a

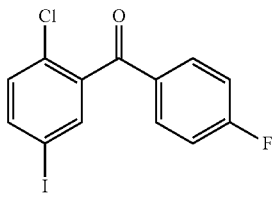

7a

Oxalyl chloride (72 g, 0.56 moles) was added to a slurry of formula 5a (100 g, 0.35 moles) and a catalytic amount of N,N-dimethylformamide (5 mL) in fluorobenzene (250 mL) over about 60 minutes at 15-25° C. under nitrogen atmosphere. The mixture was stirred at 21-25° C. After completion of the reaction, the reaction mass was concentrated to remove excess oxalyl chloride. The obtained residue was diluted with fluorobenzene (125 mL) and cooled to 15-25° C. Aluminum chloride (53.5 g, 0.40 moles) was added to this reaction mixture portion-wise while keeping the reaction mass temperature below 25° C. and maintaining it at same temperature to complete the reaction. After completion of reaction, the reaction mass was quenched into precooled dilute hydrochloric acid (5%, 1700 mL, 0-5° C.) at 5-25° C. After stirring for 60 minutes at 20-25° C., the product was extracted with methylene chloride twice (first with 500 mL, then with 250 mL). The combined organic layers were washed with 10% aqueous sodium hydroxide solution (250 mL), water (500 mL), and 10% aqueous sodium chloride solution (250 mL), sequentially. Thereafter, the organic layer was concentrated and the obtained residue was diluted with n-heptane (250 mL) and stirred to precipitate formula 7a as a white solid (105 g).

Example 8: Preparation of Formula 9a

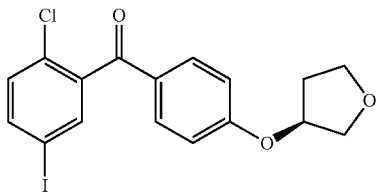

9a

A mixture of formula 7a (100 g, 0.277 mole) and (S)-tetrahydrofuran-3-ol (27.4 g, 0.31 mole) in tetrahydrofuran (260 mL) was prepared. Potassium tert-butoxide (46.5 g, 0.414 mole) in tetrahydrofuran (405 mL) was added to this mixture solution slowly over a period of 90 minutes at 2-6° C., maintaining the reaction mass at 7-10° C. to complete the reaction. Thereafter, precooled water (285 mL) was added to quench the reaction at 5-18° C. and the product was extracted twice with methyl tert-butyl ether (first with 285 mL, then with 145 mL) at 20-25° C. Thereafter, the combined organic layers were washed with 10% aqueous sodium chloride (250 mL) solution and concentrated under reduced pressure. The obtained residue was crystallized in isopropyl acetate (150 mL) to result in formula 9a as solid (90 g).

Example 9: Preparation of Formula 12a

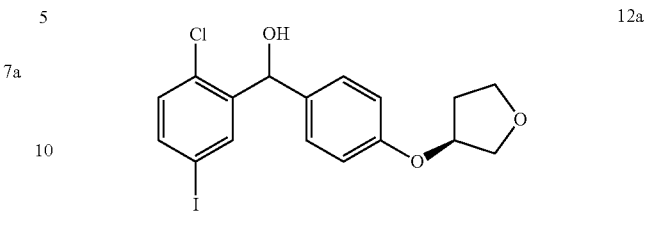

12a

Sodium borohydride (13.2 g, 0.34 moles) was added lot-wise to a solution of formula 9a (100 g, 0.233 mole) in ethanol (800 mL) at 20-25° C. Thereafter, the temperature of the reaction mass was maintained at same temperature to complete the reaction. After completion of reaction, the pH of reaction mass was adjusted to 6.5-7.5 with dilute hydrochloric acid while keeping the mass below 20° C. After stirring for 60 minutes, salts were separated out by filtration and the residue was washed with ethanol (100 mL). The obtained filtrate was concentrated and diluted with water (1000 mL). Thereafter, the product was extracted twice with methyl tert-butyl ether (once with 500 mL, then with 250 mL) at 20-25° C. The combined organic layers were washed with water (300 mL), followed by aqueous sodium chloride (10%, 300 mL) and concentrated under reduced pressure to yield formula 12a as a viscous liquid, which tends to solidify upon standing (98 g).

1H NMR (300 MHz, DMSO-d6) δ=8.0 (s, 1H), 7.64-7.60 (d, 1H), 7.21-7.17 (m, 3H), 6.87-6.84 (d, 2H), 6.16-6.09 (d, 1H), 5.85-5.84 (d, 1H), 4.99-4.97 (m, 1H), 3.89-3.72 (m, 4H), 3.08 (s, 1H), 2.51-2.50 (m, 1H)

Example 10: Preparation of Formula 12'a

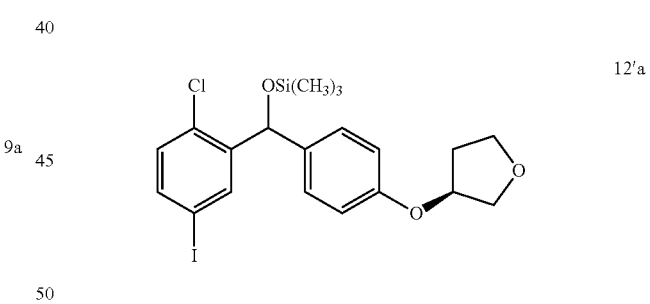

12'a

Triethylamine (52.8 g, 0.52 moles) was added to a solution of formula 12a (100 g, 0.232 moles) in methylene chloride (900 mL) at 0-5° C. Trimethylsilyl chloride (37.8 g, 0.348 moles) was added slowly to this reaction mixture over a period of 60 minutes while maintaining same temperature (0-5° C.). After completion of addition, the temperature of reaction mass was raised to 30-35° C. and stirred until the reaction completed. After completion of the reaction, the reaction mass was again cooled to 0-10° C. and diluted with water (500 mL) slowly, keeping the temperature below 15° C. After separating the organic layer, the aqueous layer was extracted with methylene chloride (250 mL). The combined organic layers were washed with water (500 mL), aqueous sodium dihydrogen phosphate (10%, 400 mL), and aqueous sodium chloride (10%, 400 mL) sequentially. The organic layer was concentrated under reduced pressure to yield formula 12'a as a viscous liquid (95 g).

1H NMR (300 MHz, DMSO-d6) δ=7.92 (s, 1H), 7.65-7.62 (d, 1H), 7.23-7.20 (m, 3H), 6.88-6.86 (d, 2H), 5.99 (s, 1H), 4.97 (s, 1H), 3.85-3.35 (m, 4H), 2.20-2.16 (m, 1H), 1.94-1.92 (m, 1H), 0.04 (s, 9H).

Example 11: Preparation of Formula 12'aa

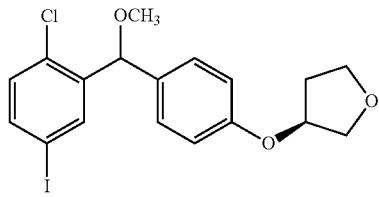

12'aa

Formula 12a (70 g) was added to methanol (350 mL) at 20-25° C. Methane sulfonic acid (23.42 g) diluted in methanol (10 mL) was added slowly to this mixture at 20-30° C., maintaining the reaction mass temperature to complete the reaction. After completion of the reaction, the pH of reaction mass was adjusted to 7.3 with aqueous sodium bicarbonate solution. Thereafter, reaction mass was concentrated under reduced pressure maintaining the temperature below 50° C. The obtained residue was diluted with water (400 mL) and the product was extracted twice with toluene (2×250 mL). The combined organic layers were washed with aqueous sodium chloride (10%, 400 mL) and concentrated to yield formula 12'aa (69 g).

Example 12: Preparation of Formula 13a from Formula 12'b

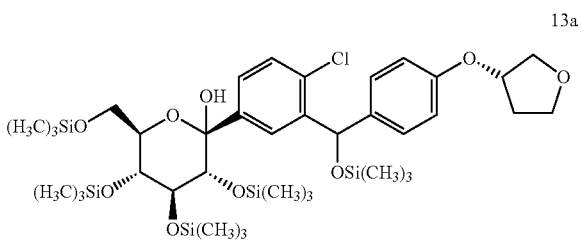

13a

Formula 12'b (50 g, 0.109 moles) was added to tetrahydrofuran (1000 mL) under nitrogen atmosphere. To this mixture, 2,3,4,6-tetrakis-O-(trimethylsilyl)-D-glucopyranone (76.8 g, 0.164 moles) was added at 25-35° C. This reaction mixture was cooled to −75 to −70° C. over a period of 30-60 minutes under nitrogen atmosphere. Then, n-butyl lithium (2.5 M in hexane, 110 mL) was added over a period of 60-90 minutes at same temperature. The reaction mixture was maintained at this temperature until the reaction completed. After completion of the reaction, aqueous 10% ammonium chloride solution was added to the reaction mass over a period of 30 minutes at −70 to −30° C. Thereafter, the reaction mixture was diluted with ethyl acetate (500 mL) and the temperature was raised to 25-35° C. The organic layer was separated, and the aqueous layer extracted with ethyl acetate (200 mL). The combined organic layers were washed with water (500 mL) and aqueous 10% sodium chloride solution (500 mL) sequentially. After separation of the aqueous and organic layers, the organic layer was concentrated under reduced pressure, maintaining the temperature below 40° C. to yield crude oil (120 g).

Example 13: Preparation of Formula 14a from Formula 13a

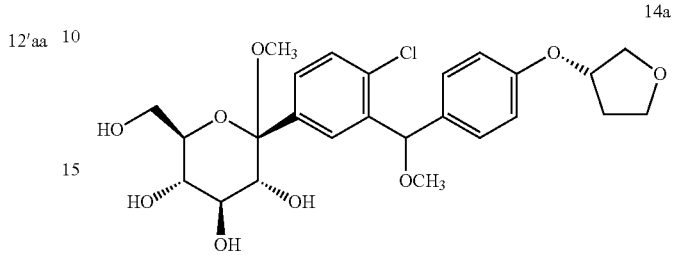

14a

Formula 13a was dissolved in methanol (1000 mL) and cooled to 0-5° C. A solution of methane sulfonic acid (12 g, 0.125 moles) in methanol (240 mL) was then added over a period of 40 minutes at 0-5° C. After the addition, the reaction mass temperature was raised to 25-35° C. and stirred over night at the same temperature. Thereafter, a saturated sodium bicarbonate solution (150 mL) was added to the reaction mass and concentrated under reduced pressure while the temperature was maintained below 45° C. The obtained residue was dissolved in ethyl acetate (625 mL) then washed with water (625 mL) and 10% aqueous sodium chloride solution (625 mL). The organic layer was separated and concentrated under reduced pressure at 40-45° C. N-heptane (250 mL) was then added and traces of ethyl acetate were distilled off to yield a foamy mass, which was recrystallized with cyclohexane and ethyl acetate to yield formula 14a as a solid (45 g).

1H NMR (300 MHz, DMSO-d6) δ=7.46-7.45 (d, 1H), 7.38-7.18 (m, 4H), 6.88-6.82 (t, 2H), 5.51-5.50 (d, 1H), 5.03-4.80 (m, 4H), 4.61-4.58 (m, 1H), 3.86-3.72 (m, 6H), 3.59-3.56 (m, 1H), 3.28-3.24 (m, 4H), 2.97-2.95 (d, 3H), 2.91-2.88 (m, 1H), 2.29-2.17 (m, 1H), 1.98-1.88 (m, 1H), 1.32-1.15 (m, 1H).

Example 14: Preparation of Formula 13a from Formula 12'a

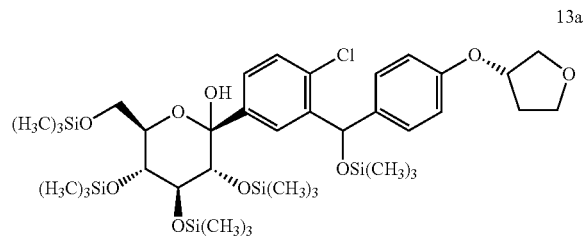

13a

Formula 12'a (15 g, 0.0298 moles) and 2,3,4,6-tetrakis-O-(trimethyl-silyl)-D-glucopyranone (20.9 g, 0.044 moles) were added to tetrahydrofuran (300 mL) at 25-35° C. under nitrogen atmosphere. This reaction mixture was cooled to −75 to −70° C. over a period of 30-60 minutes under nitrogen atmosphere. N-butyl lithium (2.5 M in hexane, 30 mL) was added over a period of 60-90 minutes maintaining the reaction mixture at the same temperature until the reaction completed. After completion of the reaction, 10% aqueous ammonium chloride solution (150 mL) was added to the reaction mass over a period of 30 minutes at −70 to −30° C. The reaction mixture was then diluted with ethyl acetate (150 mL) and the temperature was raised to 25-35° C. The organic layer was separated and washed with water (150 mL) and 10% aqueous sodium chloride solution (150 mL) sequentially. The organic layer was concentrated under reduced pressure at a temperature maintained below 40° C. to yield crude oil (32 g).

Example 15: Preparation of Formula 14a from Formula 13a

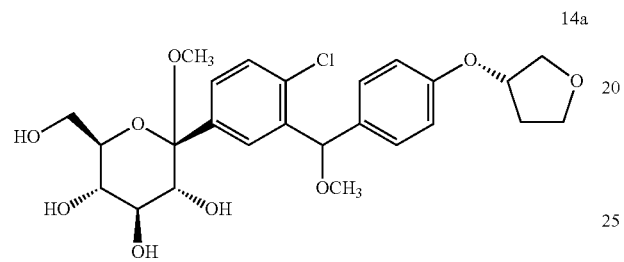

14a

Formula 13a was dissolved in methanol (200 mL) and cooled to 0-5° C. Methane sulfonic acid solution (7.66 g, 0.079 mole) in methanol (50 mL) was added over a period of 30 minutes at 0-5° C. After completion of the addition, the reaction mass temperature was raised to 25-35° C. and stirred overnight at the same temperature. Saturated sodium bicarbonate solution was added to the mixture and the reaction mass was concentrated under reduced pressure at a temperature maintained below 45° C. The obtained residue was dissolved in ethyl acetate (200 mL) and washed with water (150 mL). The aqueous layer was separated and ethyl acetate (60 mL) was added once again, and then separated. The combined the organic layers were washed with 10% aqueous sodium chloride solution (150 mL). The organic layer was concentrated under reduced pressure at 40-45° C. N-heptane (50 mL) was added and ethyl acetate was distilled off to yield a foamy mass which was recrystallized with cyclohexane and ethyl acetate to yield formula 14a as a solid (9 g).

Example 16: Preparation of Formula 13b from Formula 12'aa

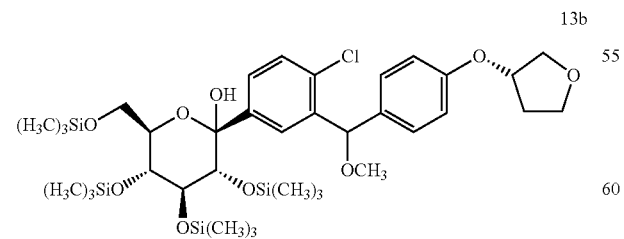

13b

Formula 12'aa (10 g, 0.0225 moles) and 2,3,4,6-tetrakis-O-(trimethylsilyl)-D-glucopyranone (15.5 g, 0.033 moles) were added to tetrahydrofuran (120 mL) at 25-35° C. under nitrogen atmosphere and then cooled to −75 to −70° C. for 30-60 minutes. N-butyl lithium (2.5 M in hexane; 25 mL, 0.062 moles) was added over a period of 60-90 minutes while maintaining the same temperature and this temperature was maintained until the reaction completed. After completion of the reaction, aqueous ammonium chloride solution (10%, 30 mL) was added to the reaction mass over the course of 30 minutes at −70 to −30° C. Thereafter, the reaction mixture was diluted with ethyl acetate (100 mL) and the temperature was raised to 25-35° C. The organic layer was washed with aqueous sodium chloride solution (10%, 30 mL) and concentrated under reduced pressure at a temperature maintained below 40-45° C. to yield crude oil (23 g).

Example 17: Preparation of Formula 14b from Formula 13b

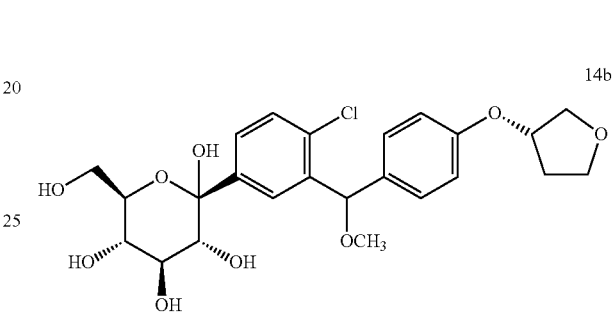

14b

Formula 13b was dissolved the methanol (150 mL) at 20-25° C. A solution of hydrochloride acid (3 mL) in methanol (20 mL) was added over the course of 30 minutes at 20-25° C. and stirred over night at same temperature. Saturated sodium bicarbonate solution was added to the mixture and the reaction mass was concentrated under reduced pressure at a temperature maintained below 45° C. The obtained residue was dissolved in ethyl acetate (200 mL) then washed with water (150 mL), aqueous sodium chloride solution (10%, 150 mL). The solution was then concentrated under reduced pressure at 40-45° C. to yield foamy mass which was recrystallized with cyclohexane and ethyl acetate to yield empagliflozin as solid (7 g).

1H NMR (300 MHz, DMSO-d6) δ=1.87-1.98 (m, 1H), 2.12-2.24 (m, 1H), 2.91-3.0 (m, 1H), 3.142-327 (d, 4H), 3.40-3.61 (m, 2H), 3.65-3.87 (m, 6H), 4.39-4.44 (m, 1H), 4.53-4.59 (m, 1H), 4.69-4.72 (m, 1H), 4.87-4.89 (m, 1H), 4.97 (m, 1H), 5.48-5.55 (m, 1H), 6.38-6.42 (m, 1H), 6.81-6.89 (m, 2H), 7.21-7.31 (m, 3H), 7.42-7.47 (m, 1H), 7.84 (m, 1H).

Example 18: Preparation of Formula 14a from Formula 13b

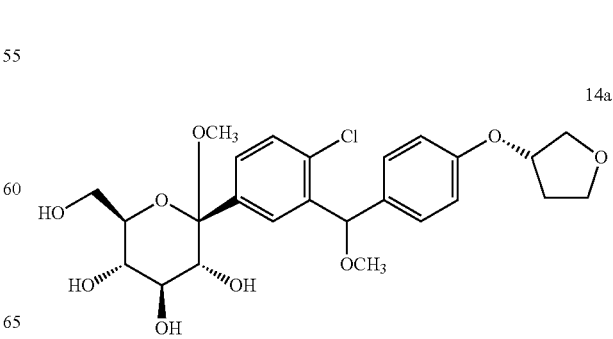

14a

Formula 13b was dissolved in methanol (150 mL) at 20-25° C. A solution of methane sulfonic acid (3 g) in methanol (20 mL) was then added over the course of 30 minutes at 20-25° C. The solution was stirred overnight at same temperature. Saturated sodium bicarbonate solution was added to the mixture and the reaction mass was concentrated under reduced pressure maintained at a temperature below 45° C. The obtained residue was dissolved in ethyl acetate (200 mL) then washed with water (150 mL) and aqueous sodium chloride solution (10%, 150 mL). The solution was then concentrated under reduced pressure at 40-45° C. to yield foamy mass which was recrystallized with cyclohexane and ethyl acetate to yield empagliflozin as solid (7 g).

Example 19: Preparation of Empagliflozin of Formula I from Formula 14a

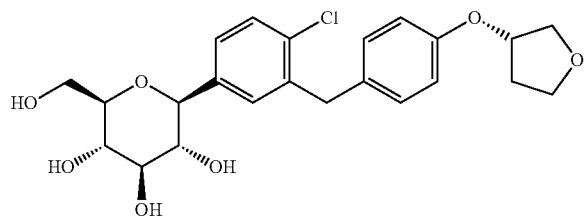

I

Formula 14a (1 g, 1.96 mole) was dissolved in a mixture of dichloromethane (10 mL) and acetonitrile (10 mL) at 25-35° C. and then cooled to −40 to −38° C. under dry nitrogen atmosphere. Triethylsilane (0.85 g, 7.3 mmole) was added then added over the course of 5-10 minutes, followed by boron trifluoride diethyl etherate (0.6 g, 4.2 mmole) while maintaining the temperature between −40 and −38° C. Next, the reaction mixture temperature was raised to 10 to 20° C. and stirred at same temperature until the reaction completed. After completion of the reaction, the reaction mixture was quenched with saturated aqueous sodium bicarbonate solution (20 mL) and diluted with ethyl acetate (20 mL). The organic layer was washed with saturated aqueous sodium bicarbonate solution (20 mL) and aqueous sodium chloride solution (10%, 20 mL). The organic layer was then concentrated under reduced pressure maintaining the temperature below 45° C. Isopropyl acetate (10 mL) was added to the residue and the mixture was heated to 45-50° C. The contents were then cooled to 25-30° C. and stirred over night at same temperature. The product was filtered and washed with isopropyl acetate (2 mL) to yield empagliflozin (0.2 g).

Example 20: Preparation of Empagliflozin of Formula I from Formula 14a

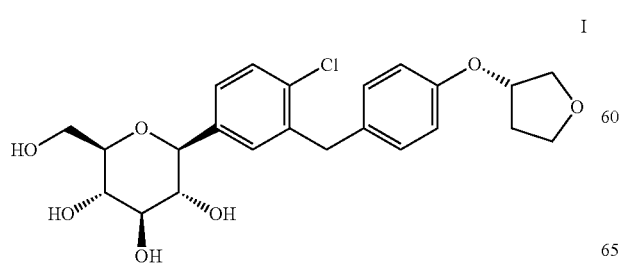

I

Aluminum chloride (5.5 g) was added to dichloromethane (18 mL) at 25-35° C. The resulting suspension was cooled to 0-5° C. under dry nitrogen atmosphere. Acetonitrile (25 mL) was added slowly to this mixture over the course of 20 minutes while holding the reaction mixture at 0-20° C. Triethylsilane (5.6 mL) was added to the above mixture over the course of 10 minutes, while maintaining the temperature at 0 to 5° C. A solution of formula 14a (5 g, 0.0098 mole) in a mixture of dichloromethane (15 mL) and acetonitrile (30 mL) was added slowly over a period of 30 minutes at 0-5° C. After the addition was complete, the reaction mixture temperature was raised to 20-25° C. and stirred at the same temperature until the reaction completed. After completion, the reaction mixture was cooled to 0 to 5° C. Precooled water (30 mL) was added slowly to quench the reaction. Thereafter, the contents were concentrated under reduced pressure maintaining the reaction mixture temperature below 45° C. The resulting residue was dissolved in dichloromethane (50 mL) and washed with 2N hydrochloric acid (25 mL) at 20-25° C. The organic layer was washed with saturated sodium chloride solution (50 mL) and the organic layer was partially concentrated to half the original volume. This mixture was stirred for 2 hours at 20-25° C. to complete crystallization. The product was filtered, washed, and dried to yield empagliflozin as a white solid (0.2 g).

We claim:

1. A process for the preparation of empagliflozin, comprising the steps of:
   a) reacting a compound of formula 12 with a hydroxyl protecting group to obtain a compound of formula 12', wherein X is a halogen and R' is a hydroxyl protecting group,

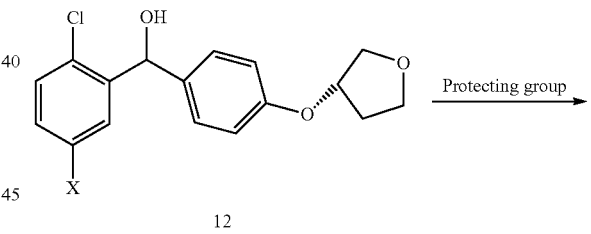

b) reacting the compound of formula 12' with a compound of formula 1 to produce a compound of formula 13, wherein $R^1$ and $R^2$ are independently hydroxyl protecting groups

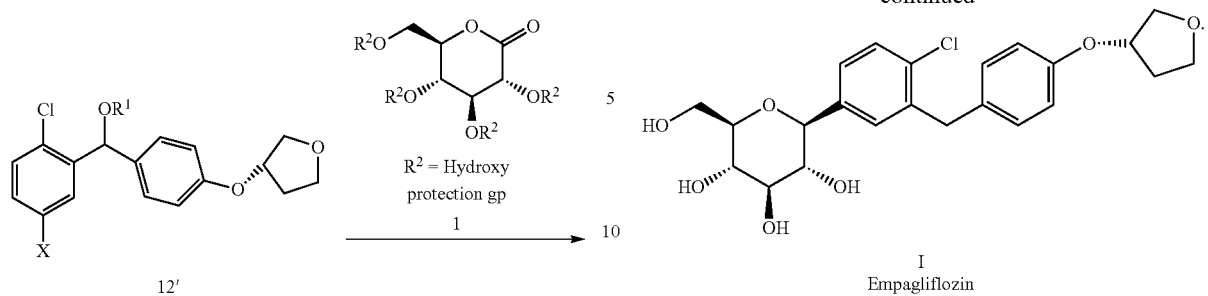

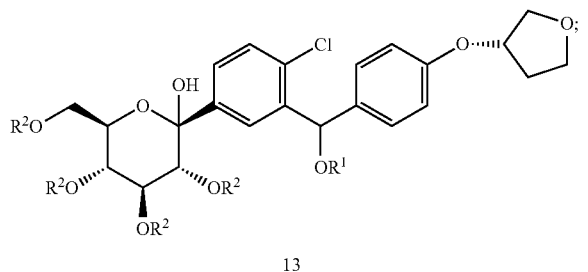

c) hydrolyzing the compound of formula 13, followed by selective hydroxyl protection to obtain a compound of formula 14, wherein $R^1$ and $R^2$ are independently hydrogen or hydroxyl protecting groups; and

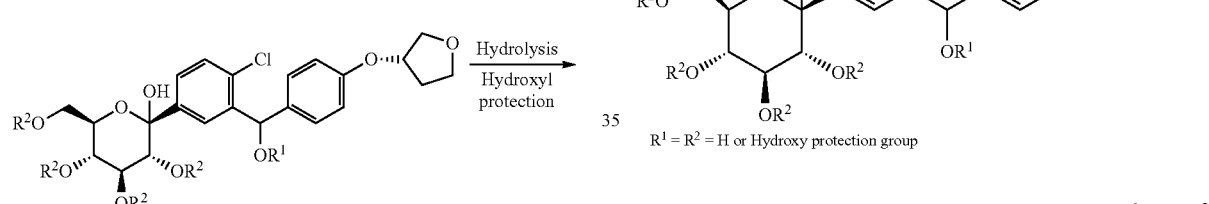

d) reducing the compound of formula 14 in the presence of a reducing agent to obtain empagliflozin of formula I

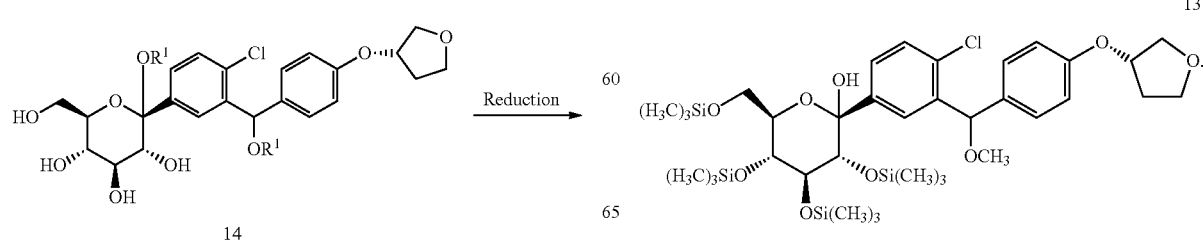

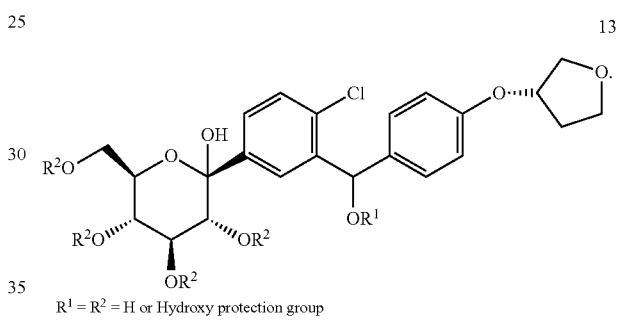

2. The process according to claim 1, wherein $R^1$ and $R^2$ are independently selected from the group consisting of benzyl, benzoyl, $C_{1-17}$ alkyl, trimethylsilyl, tert-butyl dimethyl silyl, allyl, and sulfonyl.

3. The process according to claim 1, wherein the reducing agent is selected from the group consisting of triethylsilane, boron trifluoride diethyl etherate, and mixtures thereof.

4. A compound of formula 13, wherein $R^1$ and $R^2$ are independently hydrogen or hydroxyl protecting groups

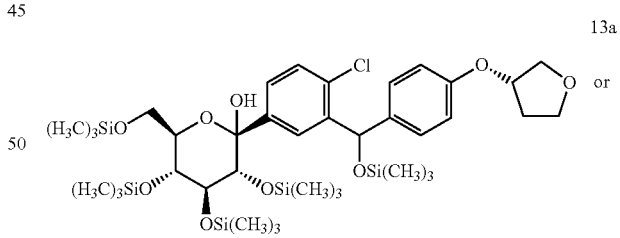

$R^1 = R^2 = H$ or Hydroxy protection group

5. The compound according to claim 4, wherein $R^1$ and $R^2$ are independently selected from the group consisting of benzyl, benzoyl, $C_{1-12}$ alkyl, trimethylsilyl, tert butyldimethylsilyl, allyl, and sulfonyl.

6. The compound according to claim 4, that is:

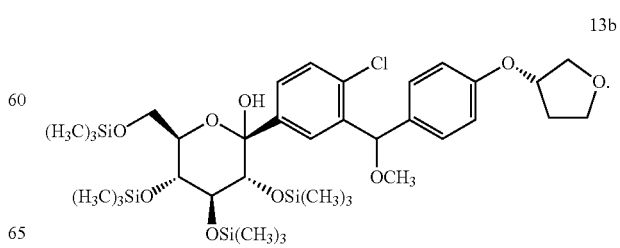

7. A compound of formula 14, wherein each R¹ is independently a hydrogen or a hydroxyl protecting group

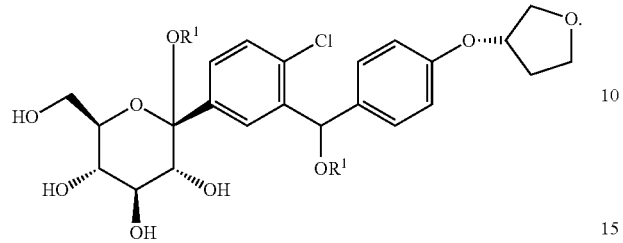

8. The compound according to claim 7, wherein each R¹ is independently selected from the group consisting of benzyl, benzoyl, $C_{1-12}$ alkyl, trimethylsilyl, tert-butyldimethylsilyl, allyl, and sulfonyl.

9. The compound according to claim 7, wherein each R¹ is independently selected from the group consisting of hydrogen and a methyl group.

10. The compound of claim 7 that is

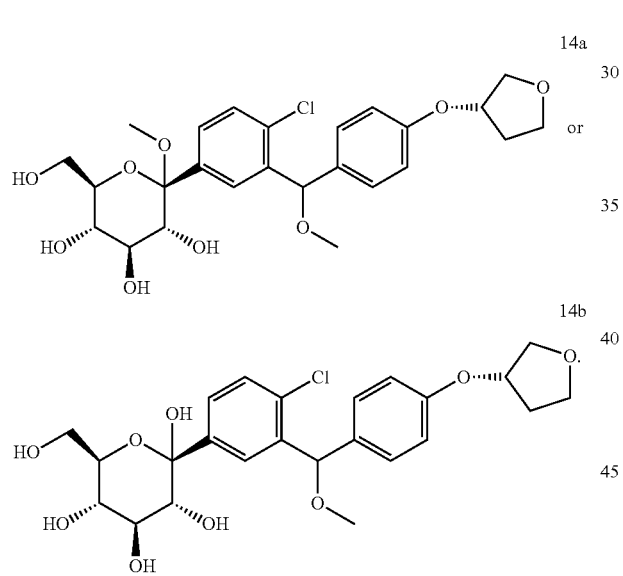

11. A process for the preparation of empagliflozin, comprising the steps of: reducing a compound of formula 14 in the presence of a reducing agent to obtain empagliflozin of formula I wherein R¹ and R² are independently hydrogen or hydroxyl protecting groups

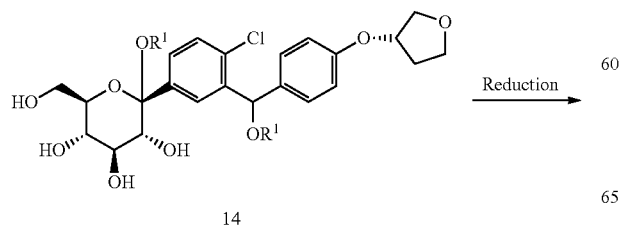

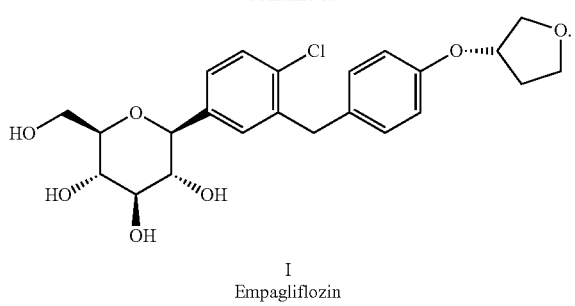

12. The process of claim 11, further comprising the step of:

before the reducing step, hydrolyzing a compound of formula 13, followed by selective hydroxyl protection to obtain the compound formula 14, wherein R¹ and R² are independently hydrogen or hydroxyl protecting groups

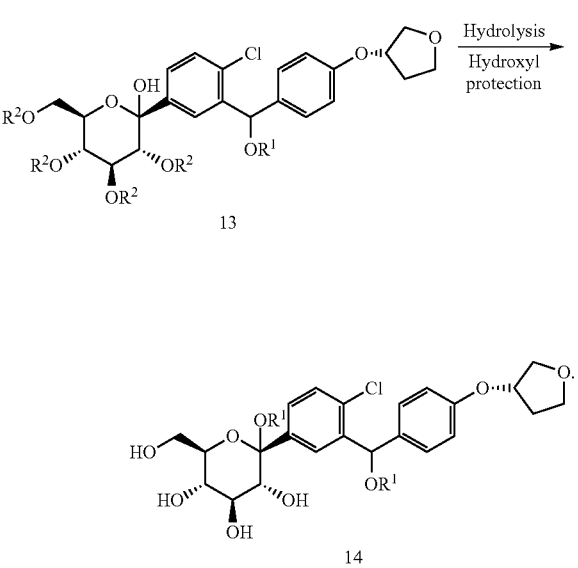

13. The process of claim 12, further comprising the step of:

before the hydrolyzing step, reacting a compound of formula 12' with a compound of formula 1 to produce the compound of formula 13, wherein R¹ and R² are independently hydroxyl protecting groups

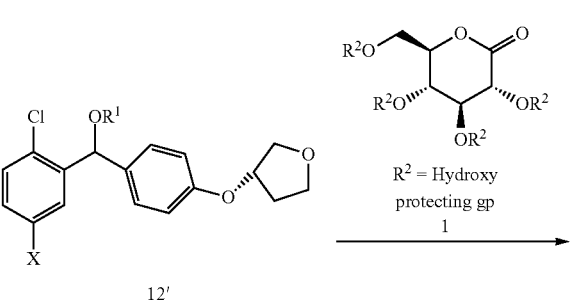

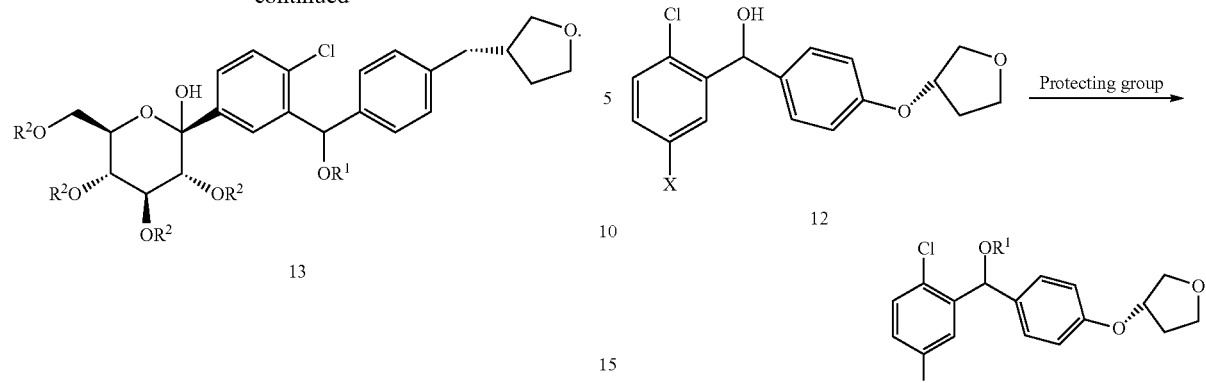
14. The process of claim 13, further comprising the step of:
Before the first reacting step, reacting a compound of formula 12 with a hydroxyl protecting agent to obtain the compound of formula 12', wherein X is a halogen and $R^1$ is a hydroxyl protecting group,
* * * * *